United States Patent [19]
Kirchner et al.

[11] Patent Number: 6,028,910
[45] Date of Patent: Feb. 22, 2000

[54] HIGH RESOLUTION AREAL TOMOSYNTHESIS

[75] Inventors: Theodore E. Kirchner, Weston; Paul Burstein, Winchester, both of Mass.

[73] Assignee: Foster-Miller, Inc., Waltham, Mass.

[21] Appl. No.: 09/008,717

[22] Filed: Jan. 19, 1998

[51] Int. Cl.[7] .................................................. G01N 23/04
[52] U.S. Cl. ............................................. 378/22; 378/21
[58] Field of Search .................................. 378/4, 21, 22, 378/23, 24, 25, 26, 27, 146

[56] References Cited

U.S. PATENT DOCUMENTS

| | | | |
|---|---|---|---|
| 5,023,895 | 6/1991 | McCroskey et al. | 378/4 |
| 5,081,656 | 1/1992 | Baker et al. | 378/21 |
| 5,287,546 | 2/1994 | Tesic et al. | 378/54 |
| 5,291,537 | 3/1994 | Mazess | 378/54 |
| 5,461,653 | 10/1995 | Parker | 378/22 |
| 5,659,483 | 8/1997 | Rhodes et al. | 702/57 |
| 5,687,209 | 11/1997 | Adams | 378/22 |
| 5,717,732 | 2/1998 | Tam | 378/4 |

OTHER PUBLICATIONS

Kirchner, T., P. Burstein, J. Youngberg and D. Waters, "Synchronous X–Ray Sinography for Nondestructive Imaging of Turbine Engines Under Load", *American Institute of Aeronautics and Astronautics, Inc.,* Copyright 1993.

*Primary Examiner*—David P. Porta
*Attorney, Agent, or Firm*—Wolf, Greenfield & Sacks, P.C.

[57] ABSTRACT

The present invention is related to laminographic apparatus and method for imaging individual layers of a multilayer structure, for example the individual layers of a composite, with capabilities for imaging in multiple dimensions or along arbitrary surfaces within the space of the structure. A source of radiation and an areal detector are moved relative to a test specimen positioned therebetween such that a magnified two dimensional image of the test specimen is obtained at the detector. A single translational pass of the test specimen through the source/detector combination provides sensitivity to patterns in the test specimen which have small scale features lying in a direction parallel to the direction of the pass. An image with sensitivity to features in two perpendicular directions is obtained by taking passes in both directions, no mechanical registration between the perpendicular passes being required. To reconstruct a point along the pass, only local mechanical registration (over for example an inch or so) between the source, test specimen and detector is required for each pass; each point being reconstructed from a predetermined number of images taken over the short distance for which local mechanical registration was required. One or more surfaces of the test specimen may be reconstructed using digitized data of the images.

40 Claims, 10 Drawing Sheets

HIGH RESOLUTION AREAL TOMOSYNTHESIS

FIELD OF THE INVENTION

The present invention is related to laminographic techniques for imaging a structure, and more particularly to such techniques for imaging individual layers of a multilayer structure, for example the individual layers of a composite, with capabilities for imaging in multiple dimensions or along arbitrary surfaces within the space of the structure.

BACKGROUND OF THE INVENTION

A composite is a structure having multiple layers of woven or unwoven fiber or weave impregnated with a polymer material such as epoxy. Composites are tailorable so that by careful selection of material for the fiber layers, the number of layers and orientation of the layers, a composite may be fabricated having a selected set of characteristics. Composites are capable of providing, for example, strength characteristics comparable to those of metals with significantly less weight and with greater corrosion resistance. These materials are therefore frequently employed in aerospace applications and in other application where material failure can have catastrophic consequences. However, in order for these materials to perform to their design capabilities, there must be no breaks or other flaws in any of the fiber layers, either as originally fabricated or in use. Consequently, acceptance criteria for these structures are quite stringent.

However, detection of flaws in modern composites, which may for example have eight to thirty-two or more fiber layers, is a difficult task, particularly since the composites are generally anisotropic (i.e., have properties that differ depending on the direction of measurement).

If parts having anomalies/defects could be found and discarded early in the manufacturing process, tremendous savings in processing and labor would result. Also, if better post-production detection techniques were available, current large margins of error for composite components could be cut, allowing less expensive, more weight efficient structures, thereby permitting the full benefits of composites to be realized.

Current inspection techniques for such flaws/anomalies include visual, ultrasound and x-ray examination. Visual examination detects any surface breaking cracks; however, internal defects cannot be discovered by visual inspection. Ultrasound techniques locate areas of internal disbonding which are parallel to the surface, such as ply separation or failure to bond. Conventional x-ray technology can in principle reveal fiber breaks and irregularities in the fiber weave. However, normal x-ray shadowgraph technique may be overwhelmed by the superposition of many different layers in complex composites.

None of these techniques can identify the specific layer containing fiber defects, a critical parameter in determining the ultimate strength of a part. Since conventional x-ray techniques produce an image showing superposition of the many different layers, the overlay image of even eight separate layers of material, each having its own characteristic weave pattern, is extremely difficult to deconvolve visually. As can be seen in FIG. 1(a), which illustrates an image of a multiple layer test specimen obtained using the best current x-ray inspection technique, discontinuities are not obvious, and the layer containing the discontinuities cannot be identified. Inspection is often difficult and painstaking. Since the weave pattern is fine, often involving spatial scales of microns, and since these x-ray techniques are usually made as contact x-ray films, allowing virtually no magnification during the x-ray image acquisition, the resulting films may have to be scanned manually under high magnification using a conventional optical microscope. While a large portion of the fiber irregularities can be detected manually, this approach is manpower intensive and therefore expensive, slow, and tedious, resulting in errors even by experienced personnel. Also, a break in a fiber can often occur at the boundary of another superposed fiber, making visual detection virtually impossible. Moreover, since current x-ray techniques utilize a film detector, the images displayed cannot be easily digitized, and thus cannot be studied with current computer based image-processing techniques. Finally, non-film detectors, which may allow digitization but which have lower spatial resolution than film detectors, will not provide sufficient data to the computer because of the low spatial resolution of the recorded images.

Two advanced image x-ray imaging techniques, computed tomography and traditional high resolution digital laminography, also present serious limitations for imaging composites. Computed tomography (CT) returns cross-sectional images of the test specimen. Because of limitations in extended data acquisition time and in the number of picture elements in the reconstructions, CT does not present a practical approach for test specimens with large dimensions and fine spatial resolution requirements which require a large set of picture elements for reconstruction.

High resolution digital laminography serves to separate the planes of the plies, and to give good information as to the structure within the plies, all consistent with a spatial scale of microns. Laminography also allows one to image any selected internal plane independent of the material above or below it, removing confusing material above or below the surface of interest so that only that surface remains, thereby allowing an arbitrary surface in the test specimen to be reconstructed from multiple digitized images of the specimen.

Traditional laminography techniques also have serious shortcomings. As it is usually practiced, high resolution digital laminography utilizes a detector which is a high-resolution, x-ray sensitive, linear array which can only detect one dimensional images, (i.e., lines) at any one instant. In traditional laminography, a test specimen is moved through a plane PP defined by a source and two end points of the linear detector. Scanning an area of the test specimen requires multiple passes of the test specimen through plane PP, a pass being defined as a single sweep of the test specimen through plane PP. Each pass generates a single area image at the test specimen. On each successive pass, the test specimen is positioned in a different preselected orientation with respect to the source and the detector. To reconstruct any small region within the test specimen, absorption measurements from all views must be referenced/correlated to an accuracy consistent with about ⅓ of the spatial resolution of the final image. Such referencing is required to determine which imaged volume elements ("voxels") of the small region correspond to which datum points along the pass. Referencing all points along the pass (i.e., global referencing). requires precise knowledge of the relative positions of the source, test specimen and detector at each point along the pass (i.e., the procedure requires global mechanical registration). In addition traditional laminography scans the test specimen multiple times, the source being at a different orientation relative to the specimen for each pass; each additional pass thus provides a different single view of each voxel along the pass. Since data from all these different passes of the same voxels must also be correlated in order to reconstruct the region, mechanical registration of each line must be maintained between the multiple passes; and since the relevant data are acquired at different times over the entire data acquisition sequence, while the small region in question is scanned multiple times, mechanical registration is required over a spatial scale equal to the entire linear displacement of the test specimen, a distance that could be many feet in length, as the test specimen is performing complicated motions relative to the source/detector.

Achieving high mechanical registration over long, and sometime complicated passes is difficult because (a) precise position measurements are difficult and expensive to achieve and (b) both the relative position and absolute position of parts over long distances and over extended time periods are affected by multiple environmental, mechanical and other conditions which may result in continuously varying (systematic) or randomly varying errors. The sum of these errors, which is generally unpredictable, is referred to as a cumulative error. Since it is difficult to know with precision the position of the source, test specimen and detector at each point along each pass, using conventional laminography, such points can be accurately reconstructed at high resolution only with great difficulty.

In sum, one drawback of traditional laminography is the inherent need for multi-pass scanning which results in a slow, time consuming process. Another drawback is the requirement for high mechanical registration over multiple, frequently spatially-lengthy passes. Because of such drawbacks, it is difficult and time consuming to achieve high resolution images of large test specimens by traditional laminography. Moreover, traditional laminography is also not readily adapted for imaging curved test specimens.

Laminographic systems used in the medical imaging field also have shortcomings. Such systems image planes in the body along the longitudinal axis, are large and execute their motions in complex Lissajous figures. The images are recorded on film under the patient, such that only one plane is imaged for each scan. Further, there is only a 2 line pair/millimeter (lp/mm) or 0.01 in. resolution limit on most such systems, because of the severe mechanical accuracy requirements. The accumulated mechanical uncertainty over the pass must be less than approximately ⅓ of this number— approximately 0.003 in.—which is a difficult and expensive mechanical constraint to meet.

Another laminographic approach, also having drawbacks, is described by Bakes et al. in U.S. Pat. No. 5,081,656 and involves rotationally steering an electrically scanned x-ray beam across a mechanically stationary test specimen and x-ray detector. The digitally processed data can then be used to reconstruct any surface within the body of the test specimen. The limitations of this technique result from the requirement that the diameter of the circle traced out by the x-ray focal spot within the beam source housing be relatively small. Tracing such a small circle may not yield sufficient angular separation of views on thicker test specimens or provide sufficiently large fields of view in larger specimens. Thus, this approach is limited to relatively small and thin test specimens, such as circuit boards. Such prior art inspection technologies are therefore of limited utility in detecting breaks, debonding/delaminations, impact damage, and other flaws/anomalies in large complex composites.

Because current inspection methods are inadequate, in order to maintain the requisite margin of error/safety, particularly in critical applications, composite structures are overdesigned and manufactured, often with two to four times the fiber layer mass that would be required in the absence of undetected anomalies. This significantly reduces the weight advantages achieved using composites and greatly increases material costs. Similar problems exist for inspecting other multilayer, multidimensional structures.

A need therefore exists for a robust, efficient inspection technique for multilayer, multidimensional structures such as complex composites, which can isolate and image individual layers of a multilayer structure irrespective of thickness or layer geometry with minimal mechanical registration requirements.

SUMMARY OF THE INVENTION

The invention involves a one-pass translational laminographic technique for studying anomalies in composites by utilizing a high resolution area tomosynthesis approach (HAT). This approach utilizes a microfocus source and an areal detector, preferably operated in magnification mode, in order to produce a two dimensional image of an area within the test specimen.

Data acquired on a single pass of the source/detector system across the specimen is used to build up/reconstruct the interior of the region which the pass encompasses. From the data acquired on a single pass, which could be many feet long, each point/voxel is reconstructed using only images of that voxel obtained over a relatively short segment of the pass, e.g., approximately an inch. Consequently, only local mechanical accuracy is required, over for example an inch or so, while the data of the reconstructed point are being acquired. Since data gathered throughout the pass need not be referenced/correlated together, except locally, there is no need for global mechanical accuracy. One pass translational laminography yields an image that shows defects whose small scale features lie predominately in one direction, parallel to the direction of the pass.

Alternatively, the approach can consist of obtaining two such passes of data, the two pass directions being perpendicular to each other. The first pass yields primary sensitivity to features lying in one direction, parallel to that first pass direction. The second pass, made in a direction perpendicular to the first pass, yields sensitivity to features lying in a second direction, parallel to the second pass direction. Since any plane pattern can be broken into two perpendicular components, two perpendicular passes provide sensitivity to all patterns which may be present in the test specimen, and thus yield a better imaging scheme than a single pass system.

If two passes are taken, these two passes can be obtained independently, such that mechanical registration need not be maintained between the two passes. Moreover, the two-pass approach requires only local accuracy during each pass.

Depending on the dimensions of the test specimen, the technique may in principle be extended to three passes, where the third pass may be made in a third direction, perpendicular to (or at the least external to the plane defined by) the other two passes, yielding sensitivity to features parallel to such third direction (the direction of the third pass generally being a function of the geometry of the test specimen).

For each pass, images are obtained on the areal detector, digitized and stored as a data set. The digitized data set of each pass can be used separately to construct an independent image for each pass, or the data sets can be integrated to produce a single image that combines the directional sensitivities of each of the individual passes.

Further, whether one or two passes are taken, any number of layers can be imaged from a single data set, permitting detection and identification of the layer and/or location of an anomaly.

To inspect larger areas, a series of such area inspections are made and joined in a mosaic to form an image of the larger area.

This invention permits a layer-by-layer examination of complex composite structures. Such a technique results in improved spatial resolution, depth resolution and inspection speed. Moreover, the use of the microfocus source and areal detection in magnification mode allows the use of a relatively simple and conventional real-time radiography system as the detector.

BRIEF DESCRIPTION OF THE DRAWINGS

FIG. 5(b) contains views illustrating back projection for the images of FIG. 5a.

DETAILED DESCRIPTION

The present invention will be more completely understood through the following detailed description which should be read in conjunction with the attached drawings in which similar reference numbers indicate similar structure.

Figure 2:
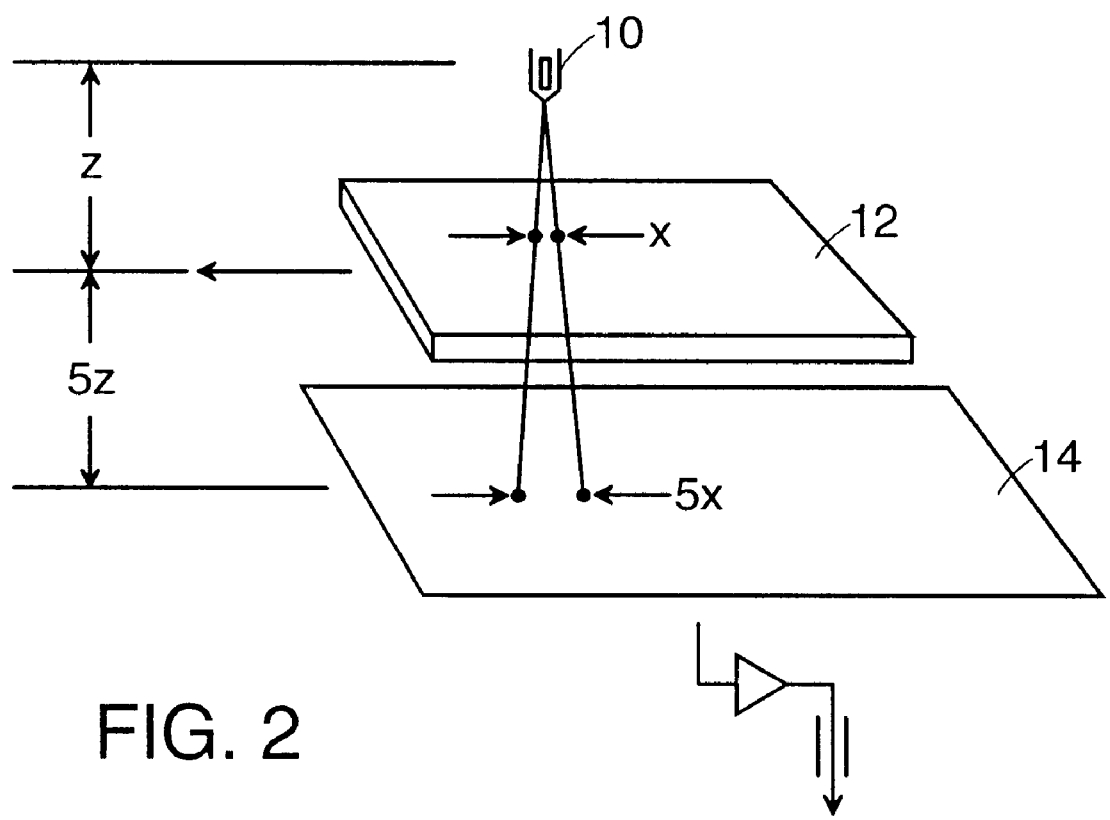
FIG. 2 is a diagram illustrating the concepts of the invention.

FIG. 2 illustrates the imaging concept of this invention. A microfocus x-ray source 10 is fixed at a distance Z above the test specimen 12, which may, for example, be of a complex composite material. A high resolution areal detector 14 is placed at a distance of, for example, 5Z below the test specimen. The relative spacing of the source, test specimen and detector determines the magnification; thus, for the spacings indicated in FIG. 2, the projection of a test specimen unit volume X, having the shape of the radiation cone penetrating the test specimen, is magnified to 5X at the detector. The system thus provides a magnified two dimensional projection image of each test specimen unit volume radiated by the source.

Figure 3:
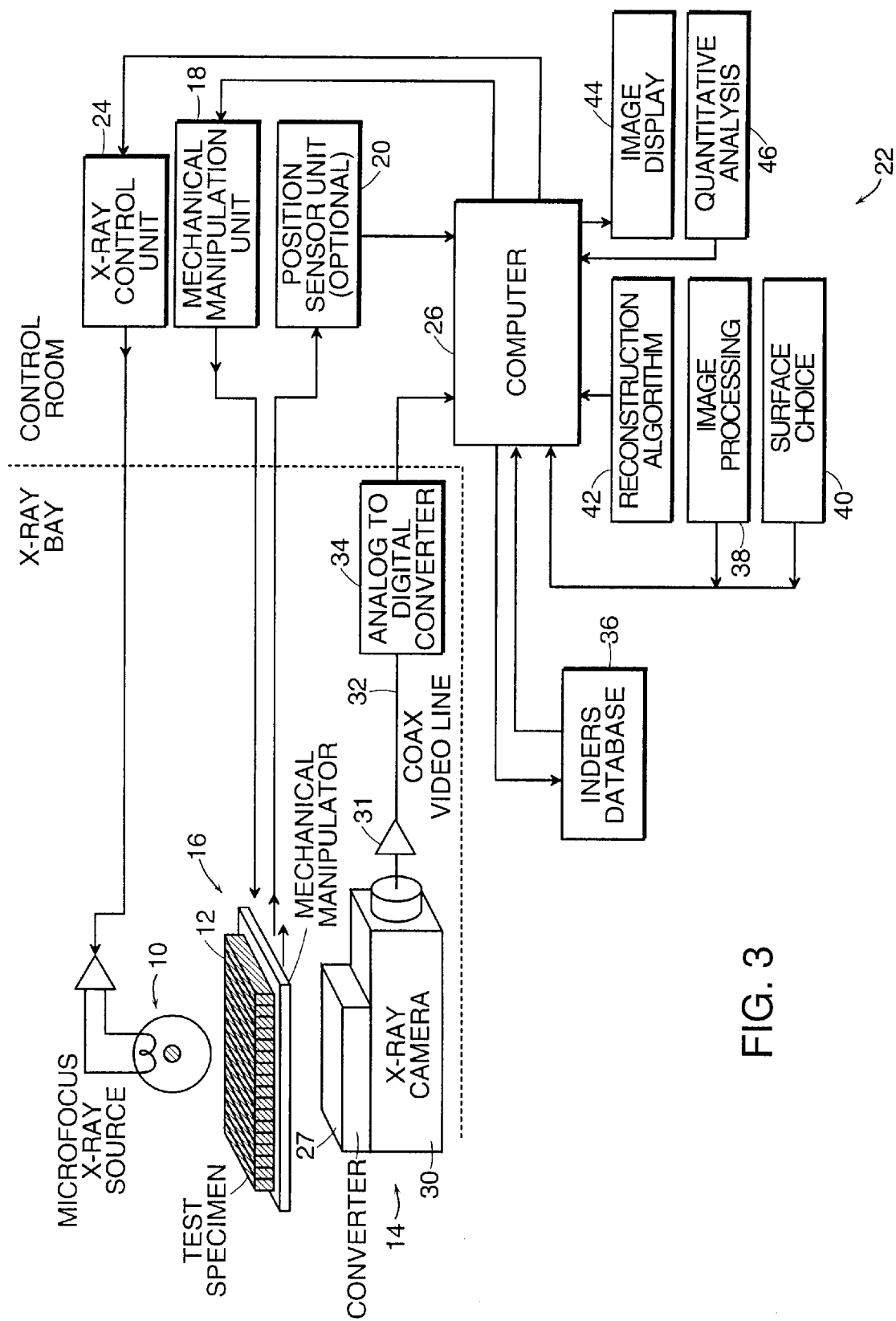
FIG. 3 is a schematic, semi-block diagram of a system for practicing the teachings of this invention.

FIG. 3 is a more detailed diagram of a configuration for a typical embodiment of the system. The key elements include a microfocus x-ray source 10, an x-ray areal detector 14, a mechanical manipulator 16, a mechanical manipulator control unit 18, a position sensor unit 20 and processing electronics 22. More particularly, the microfocus x-ray source 10 is actuated by an x-ray control unit 24 which is controlled by computer 26. For a configuration where the test specimen is moving and the source/detector combination is stationary, below the source 10, the test specimen 12 is placed on mechanical manipulator 16 which is actuated by the mechanical manipulation unit 18 under control of computer 26. To achieve more information on instantaneous test specimen positions, a position sensor unit 20, may optionally be utilized. Position sensor 20 may be a laser interferometer or other position sensor known in the art. In an alternative configuration, where the test specimen is stationary and the source/detector combination is moving, a suitable mechanical manipulator is used to move the source/detector combination as a unit instead of the test specimen. Areal detector 14 includes an x-ray-to-visible light converter 28, which is the front section of an x-ray camera 30. An output from camera 30 is connected through an amplifier 31, coax line 32, and analog-to-digital converter 34 to computer 26. Converter 28 converts x-rays to visible light, and camera 30 images and converts the visible light image to an analog video signal. Analog-to-digital converter 34 digitizes the images from the camera and outputs the digital information to computer 26 to be stored as a data set. Computer 26 also receives an input from a stored database 36 which organizes the data set. Preferably, the database can arrange the data so that a particular layer can be queried digitally. An Integrated Non-Destructive Evaluation Data Reduction System Database, [INDERS], originally developed by NASA's Marshall Space Flight Center, is an example of such a database, where data are organized in a way permitting a data search to be rooted in the geometry of the test specimen. For example, with an INDERS database, information on a particular portion of a particular layer of a wing of an aircraft is stored and can be searched for features of the composite such as an anomaly or other relevant parameter, e.g., the distance between adjacent fibers. Database 36 optionally can receive information from the computer about the specimen, for example, storing information about a discovered anomaly so that it can be retrieved later. Further, the computer 26 receives inputs from image processing/data conditioning unit 38, surface choice unit 40, a reconstruction algorithm 42 and quantitative analysis algorithm 46. Data conditioning involves removal of all instrumental effects from the absorption measurements which includes: normalization of the data for temporal variations, interpolations of data for missed views, (a "view" being an assembly of a subset of absorption measurements that are arranged to present a single image of the region to be reconstructed), removal of electronic "glitches" and noise in the data acquisition system. Surface choice unit 40 allows a selection of a particular surface(s) along which to perform image reconstruction using the algorithm described below. With an INDERS-like database, data corresponding to such surfaces can be easily accessed. A quantitative analysis algorithm 40 is used to analyze data for defects or for other purposes. The image processing/conditioning, surface choice, reconstruction algorithm and quantitative analysis units could be one unit or separate units and/or could be functions performed under software control, within computer 26. Computer 26 outputs information and/or signals to an image display unit 44 which displays the surfaces(s) selected.

The x-ray source for preferred embodiments is a microfocus source, for example, a 160 kV source having a 10 $\mu$m size spot. A microfocus source, radiating energy from a very small spot minimizes geometric unsharpness, (defined as D*(S1/S2), where D is the size of the x-ray source focal spot, S1 is the distance from the point imaged to the detector (distance 5Z in FIG. 2), and S2 is the distance from the source to the point imaged) (distance Z in FIG. 2), allowing a more precise image of each point. Thus, for any particular geometry of the source, test specimen and detector, minimizing the spot size of the source sharpens the image of each point. Therefore, rather than presenting a blurry image, a source having a sufficiently small focal spot size allows for a geometric configuration, (i.e., chosen magnification and resulting geometric unsharpness), which yields a finer image plane resolution than would normally be associated with other elements in the imaging chain. Another consideration which drives the source requirements is the radiation's ability to penetrate the test specimen and provide good signal to the detector. The source can be any type of radiation which can penetrate the thickness of the particular test specimen. Thus, while x-rays are utilized for the preferred embodiment, depending on the type of material and the thickness of the test specimen, different sources of radiation, such as gamma, or neutron radiation may be suitable.

For good depth resolution and plane/surface isolation within the test specimen, the x-ray beam should have a set of substantially non-parallel rays passing through each point on a single pass, i.e., the angular width of the x-ray beam should be large. The smaller the angular width of the x-ray beam cone, the more nearly parallel the paths of the x-rays impinging on the test specimen. Taking this to the extreme, a parallel-ray x-ray beam presents no difference in angle over the test specimen during data acquisition for a single pass. In such a case, the laminographic approach would not work, because it depends on the angular differences in back-projection to isolate the planes and blur out the material on either side of the plane of interest. In other words, depth resolution becomes better as the angular width of the x-ray beam cone increases, such that layers which are closer together can be resolved better with a wider beam. A microfocus source can produce a wide angle, typically on the order of 30–42°, (impinging on multiple test specimen points simultaneously), thus providing sufficient angular width to resolve layers which are close together. The x-ray detector is an areal detector which can acquire images, digitize them and send them on to a digital processing system in real time. At the most fundamental level, the x-ray detector is simply a conventional real-time radiography system (essentially to an x-ray camera which has an output connected to a video line) with a digitizer connected to its video output.

The x-ray detector is generally the limiting factor in determining the spatial resolution of the overall system. X-ray areal detectors usually have spatial resolutions of 2 to 3 lp/mm. This spatial resolution is coarse relative to the 6 to 10 lp/mm that is required for composites. Since the x-ray detector must have intrinsic spatial resolution consistent with the geometric unsharpness and overall spatial resolution requirements, the system must utilize a microfocus source and magnification to assure the required spatial resolution. The areal detector used for a preferred embodiment is a high resolution areal x-ray camera developed by the Air Force/Lockheed, which camera is described in "Corrosion Detection and Characterization Using High Resolution Real-Time Radiography", Bueno, et al., 41st International SAMPE Symposium and Exhibition *Society for the Advancement of Material and Process Engineering* (Mar. 25–28, 1996), but other suitable areal detectors may be used. The image output by the camera is a 1024×1024 array for an illustrative embodiment, with the coverage on the test specimen for this geometry being approximately 2 to 3 sq. in. per frame. There are other ways of getting an x-ray to interact and be ultimately recorded electronically. For example, a direct conversion can be achieved in a solid state detector array, where the radiation is converted into electrons which are then accelerated through channel plate(s) or through fields in space. The converter can be any of the myriad choices of commercial x-ray conversion screens, e.g., Trimax, or a custom high efficiency/high stopping-power x-ray down-conversion glass. The digitizer used is a 16 bit or higher A/D, although such high signal resolution may not be necessary in all cases.

Figure 4:
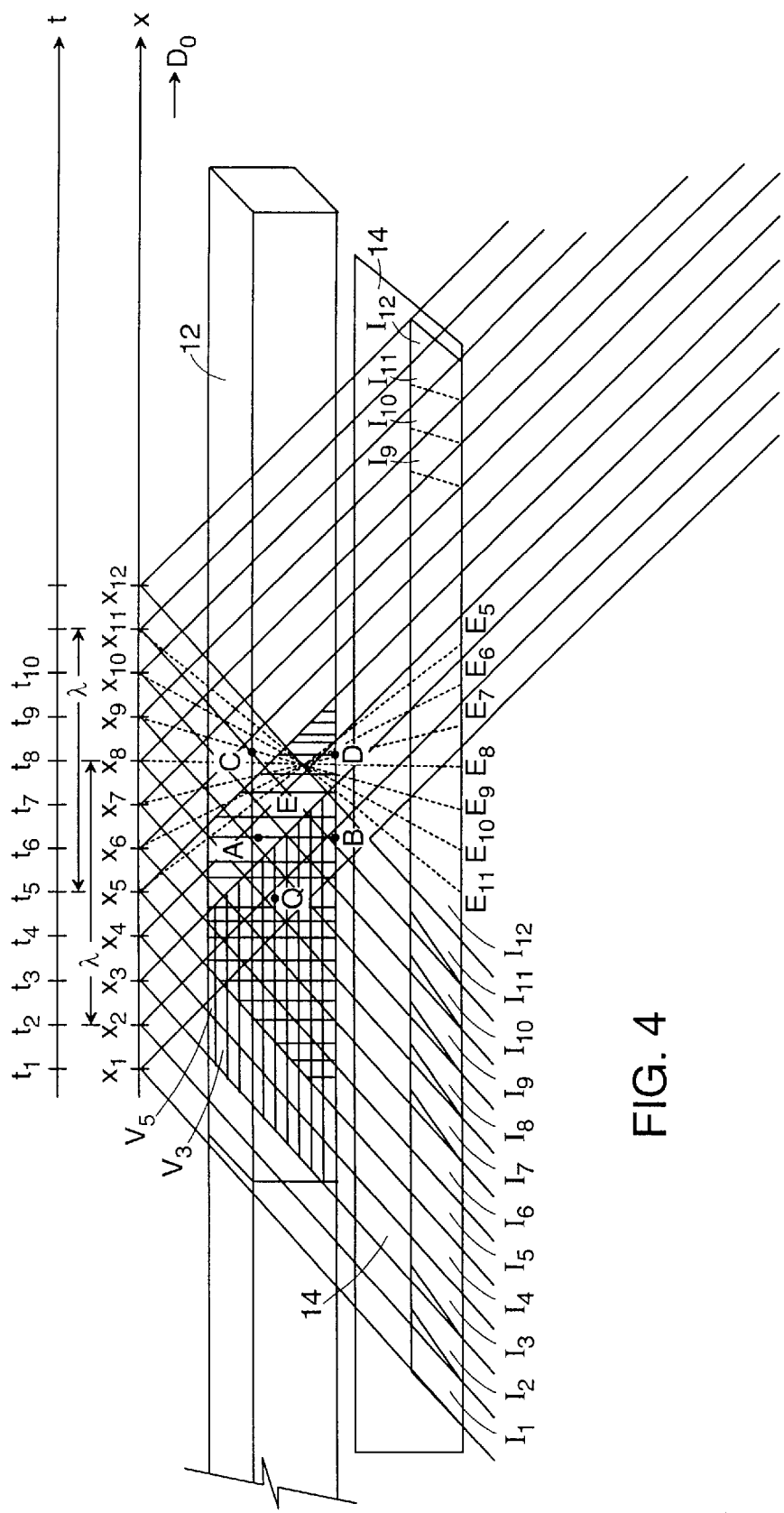
FIG. 4 is a perspective diagram illustrating an imaging process according to the invention.

The single pass of the test specimen is achieved by the relative motion between the test specimen and the source/detector combination (SDC). Thus, for example, the test specimen may move to the left and the SDC remain stationary, or, alternatively, the test specimen may remain stationary and the SDC move to the right (the case that is illustrated in FIG. 4). As the test specimen moves relative to the SDC, the source, at each instant in time, radiates each point on the test specimen from a different angle. In order to reconstruct a specified region of a test specimen, for each point in the region, 10 to 20 exposures are typically made, such that each point is imaged from 10 to 20 different angles. For purposes of illustration, FIG. 4 shows test specimen 12 being composed of a plurality of points, only points A, B, C, D, E and Q of which are labeled. At each instant in time $t_n$, source 10 is at a different position $X_n$ and a magnified 2-D x-ray image $I_n$ of a unit volume $V_n$ of the test specimen is projected onto the areal detector below. As the source 10 moves from position $X_1$ to position $X_{12}$, unit volumes $V_1$, $V_2$, $V_3$, $V_4$, $V_5$, $V_6$, $V_7$, $V_8$, $V_9$, $V_{10}$, $V_{11}$, $V_{12}$, are radiated in turn (only unit volumes $V_3$, hatched with horizontal lines, and unit volume $V_5$, hatched with vertical lines, are shown) producing respective magnified images $I_1$ through $I_{12}$ of the unit volumes on the detector below. Successively imaged unit volumes overlap, such that their common points are imaged multiple times, each time from a different angle, (i.e., only unit volume $V_3$ and $V_5$ are shown as having some overlapping points, shown by cross hatching, which indicates that these common points are imaged from position $X_3$ at time $t_3$ and $X_5$ at time $t_5$). Point E, which is a common point to radiated unit volumes $V_5$ through $V_{11}$, is imaged seven times from seven different positions $X_5$ through $X_{11}$ producing seven different image points $E_5$ through $E_{11}$, on the detector 14, each imaged point obtained at a different angle. In order to reconstruct point E, the multiple images, $E_5$ through $E_{11}$, of point E are backprojected as described below. The source can be actuated to radiate at discrete times or it can continuously radiate, provided that the integrated displacement of the source during the data acquisition period for that view is less than the acceptable local mechanical error. For detectors whose dimensions allow detection of a magnified image of the whole test area of the test specimen while the detector is stationary, the relative motion need only be between the source and the test specimen. On the other hand, detectors whose dimensions are smaller, imaging only a few magnified unit volumes at any time, must move along with the source.

Figure 5A:
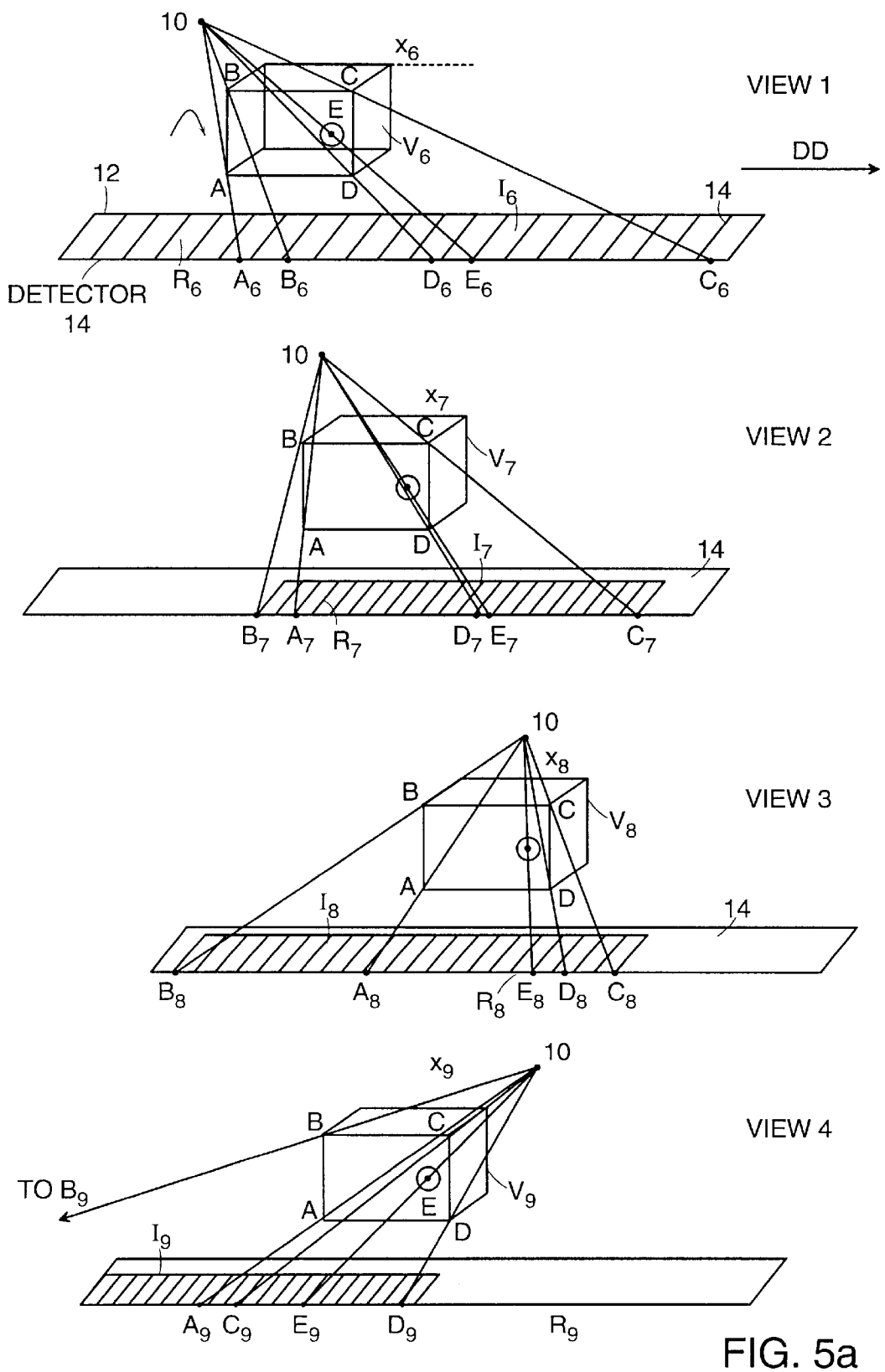
FIG. 5(a) contains four views illustrating four images of five points in a test specimen.

FIGS. 5(*a*)–5(*c*) illustrate reconstruction of a single point in a single plane by backprojection. In FIG. 5(*a*), views 1–4 illustrate only the portions of actual unit volumes $V_6$–$V_9$ which share in common points A through E and show only portions of images $I_6$ through $I_9$ which image points A through E as SDC 10/14 travels from position $X_6$ through $X_9$ in direction DD. In each one of images $I_6$ through $I_9$, points A–E can be seen projected in different locations on the detector. In view 1, the SDC 10/14 is at position $X_6$, and points A through E of volume $V_6$ are imaged as points $A_6$ through $E_6$ on the detector. In view 2, when the SDC 10/14 is in position $X_7$, points A through E of volume $V_7$ are imaged as points $A_7$ through $E_7$. Similarly, when the SDC 10/14 is at positions $X_8$ and $X_9$, points $A_8$ through $E_8$ of volume $V_8$ and points $A_9$ through $E_9$ of volume $V_9$ respectively are imaged. For each imaged point, computer 26 stores the respective attenuation data. Thus, for point E, computer 26 stores attenuation data $E_6$, $E_7$, $E_8$ and $E_9$, corresponding to the four views shown in FIG. 5(a). Similarly, computer 26 stores attenuation data $A_6$ through $A_9$, $B_6$ through $B_9$, $C_6$ through $C_9$, and $D_6$ through $D_9$, corresponding to points A through D respectively.

Figure 5B:
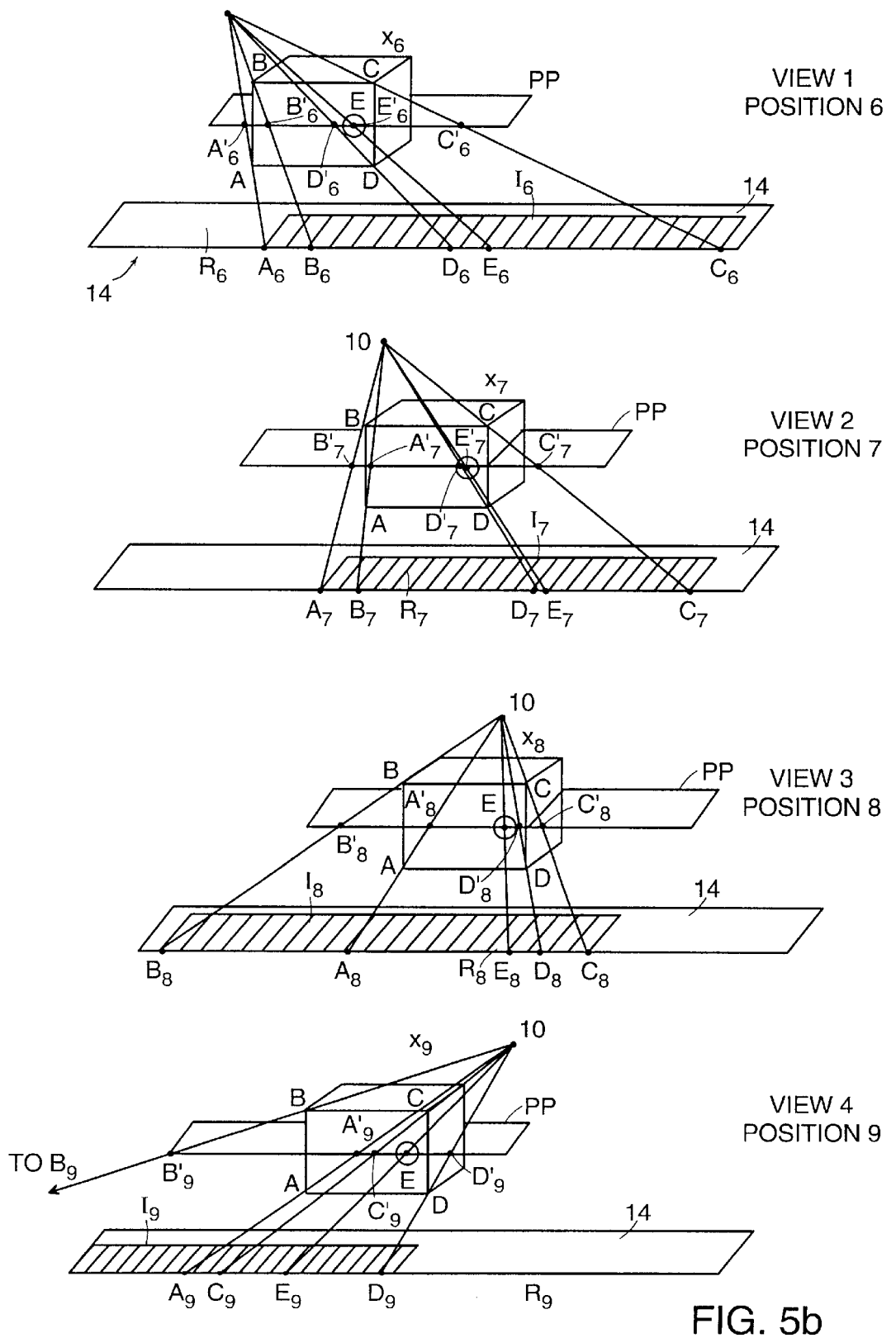
Figure 5C:
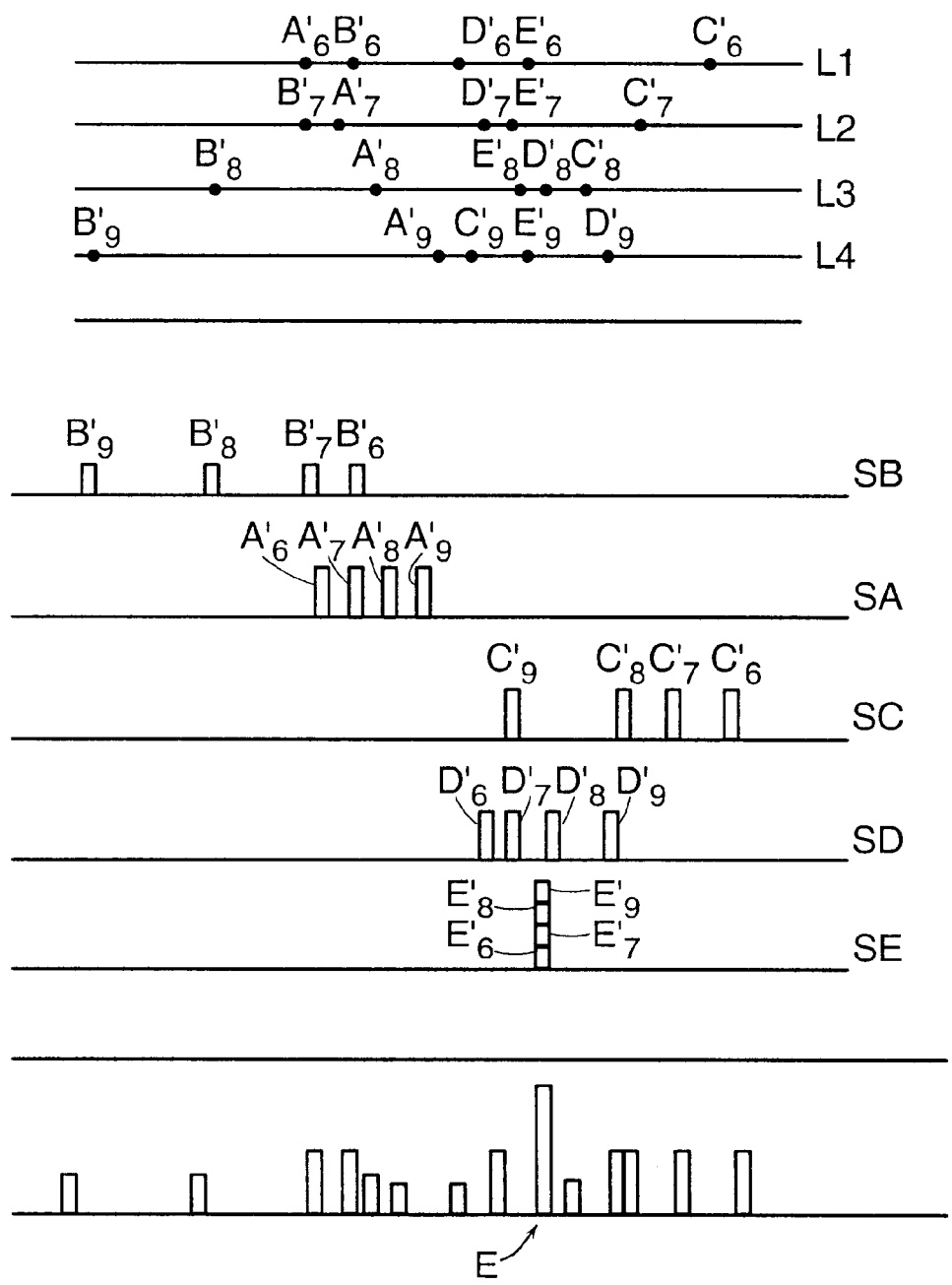
FIG. 5(c) contains graphs useful in connection with FIGS. 5(a) and 5(b).

In order to reconstruct a particular plane of the test specimen 12, each tiny volume element or voxel/point in the plane is reconstructed using the multiple views $I_n$ which imaged that voxel or point. Reconstruction of each point is achieved through the process of backprojection using attenuation data of that voxel, obtained from images of the voxel taken from each of the different angles. For purposes of illustration, FIG. 5(b) shows reconstruction along plane PP through point E discussed in FIG. 5(a); of the five points shown, and point E in plane PP is shown imaged, and only point E will be reconstructed using views $I_6$ through $I_9$ which imaged point E. For the test specimen, points A and D are in one plane, points B and C are in a different plane, only point E is the plane of interest. The first view in FIG. 5(b) shows attenuation data $A_6$ through $E_6$ backprojected to plane PP in the direction of position $X_6$, to produce layout $L_1$, shown in FIG. 5(c). The second view in FIG. 5(b) shows attenuation data $A_7$ through $E_7$ backprojected to plane PP in the direction of position $X_7$, to produce layout $L_2$, shown in FIG. 5(c). Similar projection is done for the views from positions $X_8$ through $X_9$ to produce layouts $L_3$ and $L_4$. In order to image point E, attenuation data $E_6$ through $E_9$ are aligned by shifting the attenuation data in layouts $L_1$, $L_2$, $L_3$ and $L_4$ by $X_1$, $X_2$, $X_3$ and $X_4$ respectively. All the positions of attenuation point A on the layout graphs can be seen in summation graph SA. All the positions of attenuation point B on the layout graphs can be seen in summation graph SB. Similarly, summation of attenuation points C, D and E can be seen on layout graphs SC, SD and SE respectively. By superposing all the attenuation points graphically, it can be seen that attenuation data of point E, which were aligned, add up to a large pulse, while attenuation data of points A through D, which were not aligned, do not add constructively, i.e., focus to a point. Therefore, points in the plane of interest PP, i.e., point E, will be seen more clearly, then points off this plane, i.e., points A, B, C, D, which will be blurred. Thus, through the process of backprojection, features in a selected plane can be imaged, points on the selected plane being co-focused, while points on planes below and above the selected plane are de-focused and blurry.

The local area over which there must be good mechanical registration is defined between two positions: the first position is the position which the SDC assumes (if the test specimen is stationary) when a first exposure of the point of interest is made, the second position is defined as the position of the SDC where the last exposure of that same point in interest is made. With reference to FIG. 4, where point E is imaged in views $I_5$ through $I_{11}$, reconstruction of point E using these images requires mechanical accuracy from position $X_5$ to position $X_{11}$, a total distance of $\lambda$. Similarly for point Q, which is imaged in views $I_2$ through $I_8$, mechanical accuracy need only be maintained from position $X_2$ to $X_8$, a distance of $\lambda$. Thus, since $\lambda$ is usually small—an inch or two positional uncertainties on the order of 0.001 in, over such small distances are well within the capabilities of conventional hardware.

Important factors for the degree of separation between reconstructed planes involve the range of angles over which the exposures are obtained, and the precision of knowledge of the positions at which the component exposures were made. In order to be able to image planes which are closer together, the exposures must be taken with a higher range of angles, and there must be higher precision of the relative position of the source/test specimen/detector, at which the exposures are made. Accuracy is achieved through the use of fine, spatial-scale fiducial markings: these are typically recognizable intrinsic features such as individual fibers or sharp edges. In regions devoid of such intrinsic features, external fiducials may be attached, etched, or otherwise bound to the test specimen, but such ancillary measures are less desirable. An image processing algorithm identifies and locates the fiducial feature. The position of the fiducial feature in each exposure provides information from which the relative position of the source, test specimen and detector for that exposure can be deduced. As previously indicated, knowing the relative position is crucial for backprojection and therefore for reconstruction of one or more planes.

A single pass of the test specimen produces an image with sensitivity to defects whose small scale features lie predominantly in one direction, parallel to the pass direction, where a typical feature might be a standard line-pair resolution gauge. Good depth localization, i.e., good spatial resolution in a direction perpendicular to the laminate, will achieve its desired maximum only for the component of features which lie primarily along the direction of the pass, i.e., where the spatial variations are highest in a direction parallel to the pass direction. For features which lie in a direction predominantly perpendicular to the pass, the spatial resolution will be very poor, because the angular extent of the projection of the pass in that direction is relatively small.

Figure 6:
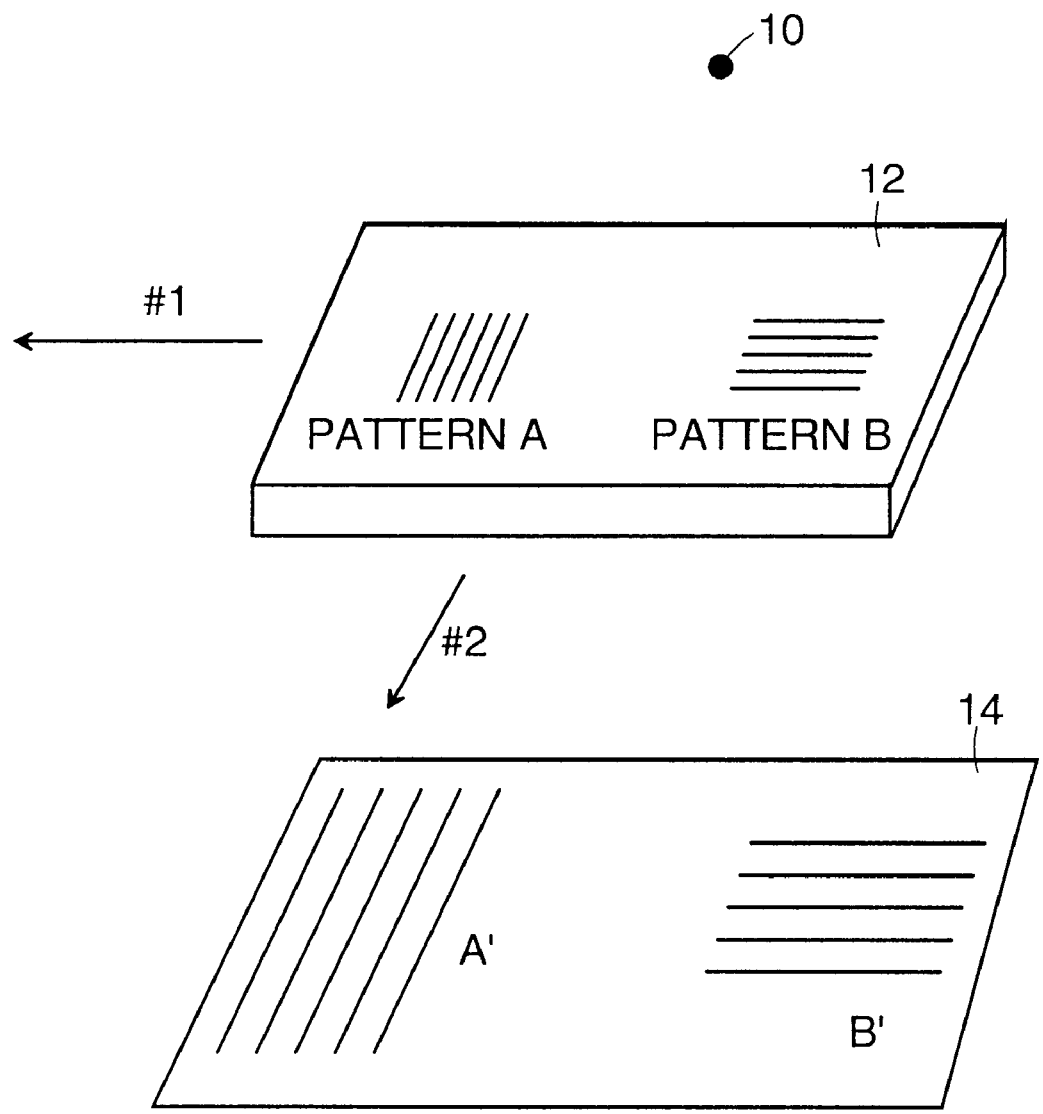
FIG. 6 illustrates two perpendicular passes in accordance with the teachings of this invention, each pass having sensitivity in a direction parallel to the direction of the pass.

For example, as seen in FIG. 6, a test specimen having pattern A on one side and pattern B on the other side is scanned twice, pass 1 being perpendicular to pass 2. Because pattern A can be described as a series of features, i.e., a set of alternating light and dark lines, only a pass in the direction of pass #1, across the lines, can detect the features of pattern A. Depth information about pattern A is not gained by scanning pattern A in the direction of pass #2. Similarly, in order to detect pattern B, one must scan across pattern B, which is in the direction of pass #2.

To obtain an image with sensitivity to features in both directions, two perpendicular passes are taken. The second pass will yield good depth localization for those features whose directions are primarily parallel to the direction of the second pass. These two passes can be analyzed individually or correlated geometrically by feature-matching, i.e., by use of precision fiducials. Two passes are sufficient to image any features, since all features can be considered as being composed of two orthogonal components, one in each of two perpendicular directions.

If the geometry and dimensions of the test specimen require it, the technique may be extended to three passes, where the third pass may be made in a third direction, which has a major component perpendicular to the other two passes, yielding sensitivity to features parallel to such third direction.

Figure 7A:
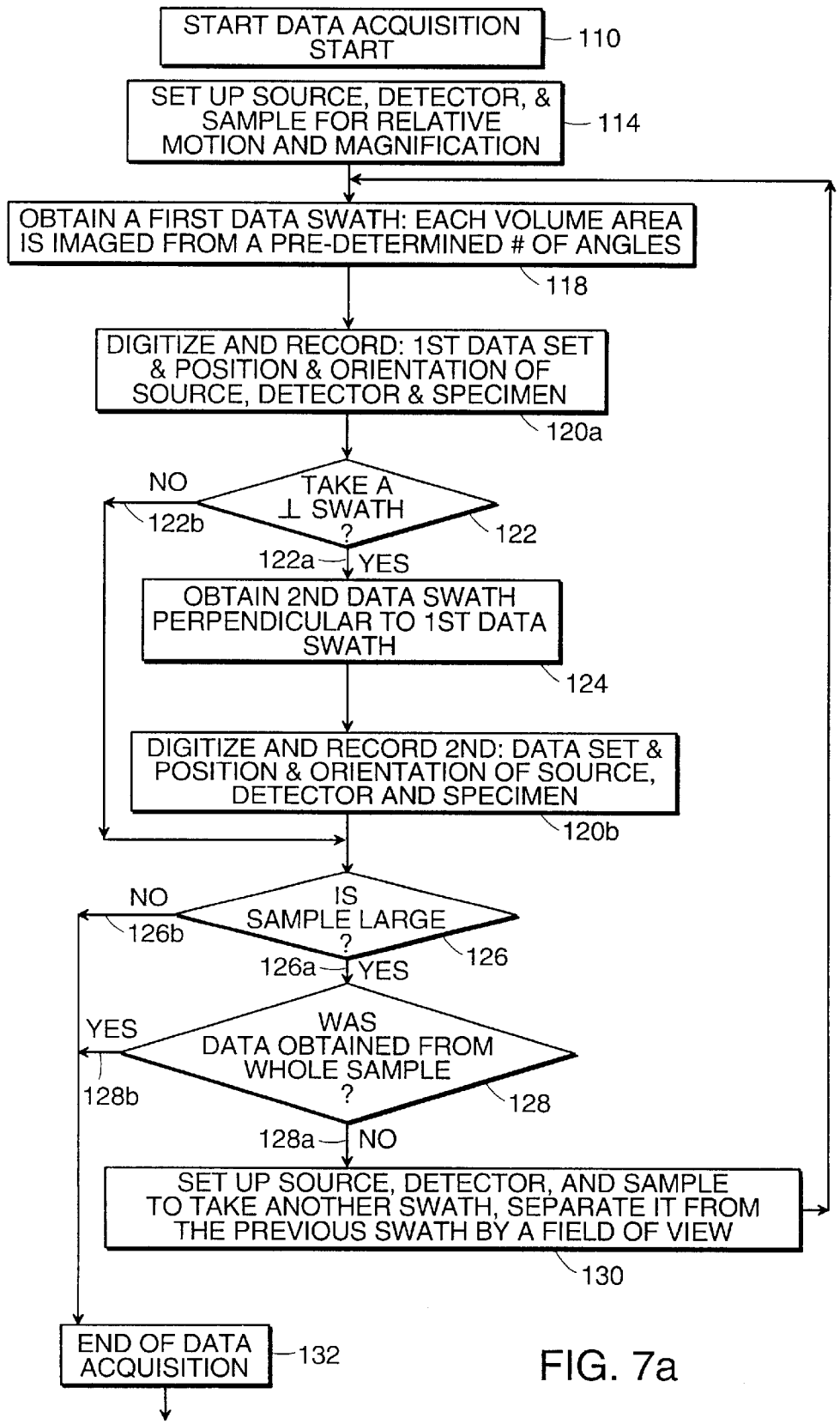
FIGS. 7(a) and 7(b), when combined, form a flow diagram for an illustrative method of practicing the teachings of this invention.

FIGS. 7(a) and (b) together are a flowchart illustrating the method according to the invention. The method can be described as having three major steps. First, data is acquired in a data acquisition step; second, the data are conditioned; and third, an image is reconstructed.

The first step, data acquisition, starts with step 110, and is composed of five substeps, ending at substep 312. During the first substep, (step 114), the x-ray source and areal detector are set up with the test specimen in a configuration that yields proper magnification and provides for relative motion between the test specimen and the source-detector combination. The second substep (step 118) includes obtaining a first data pass which comprises acquiring data by moving (for instance) the test specimen in one direction through the SDC. (Alternatively, the SDC could be moved across the test specimen). Data can be taken periodically as the source moves relative to the test specimen, or, in the alternative, stepped movement can be provided between the SDC and test specimen, with data being taken at each step. Because of the time required for taking an image, stepped movement is currently preferred to prevent blurring. Each point of the test specimen is imaged from a predetermined number of different angles to obtain the predetermined number of views. The third substep (step 120a) is a data processing step which is described below. Decision step 122 then determines if an additional pass is to be taken and, if so, branch 122a is taken leading to the fourth substep (step 124). This step, which is required only if the specimen has features to be scanned at an angle to the initial pass, involves obtaining a second data pass by running the test specimen in a direction perpendicular to the initial data pass. If a second data pass is obtained, the second data pass is processed (step 120b), as described below. If a second pass is not taken (decision 122, branch 122b), the operation jumps to step 126, described below. For imaging a small test specimen, (decision 126, branch 126b), these two passes are sufficient, and the process jumps to the end of the data acquisition step (step 132). If the test specimen is large (decision 126, branch 126a), a fifth substep (step 130) is necessary. Step 130 includes setting up the system to take a series of parallel first passes (steps 118, 120a); each of the series is separated by the field-of-view on the test specimen, i.e., such that the x-ray cone produced during a first pass and the x-ray cone produced during a second pass intersect at the surface. Optionally, (decision 122a), a series of second passes, (step 124 and 120b), separated by the field-of-view can be taken. After each additional first pass, and optionally second pass, if the test specimen is not completely covered, (decision 128, branch 128a), steps 130, 118, 120a, 122, 124, 120b are repeated. If these passes cover the complete test specimen, (decision 128, branch 128b), the data acquisition step is done (step 132). From the two perpendicular pass, two uncorrelated depth maps of features are obtained, the maps can be considered to contain the orthogonal components of the features, i.e., the components of the features in the two pass directions which, together, contain all features no matter what their preferential directions within the plane. Other scanning sequences than that shown in the Figure are also possible. For example, successive first data passes would be completed followed by any required second data passes, rather than interspersing the data passes in the two directions.

During these passes, for each relative position of the source, test specimen and detector, the following data processing (step 120a and 120b) should be done: a) Digitize and record the x-ray image data; b) Digitize and record the positions and orientations of the source, test specimen and detector; c) Digitize and record the intensity of the normalization detector (i.e., x-ray reference detector), if necessary. Each of the digitization and recording steps above must be taken with a knowledge of the appropriate accuracy, error bar, significance of the data etc. Also, the digitization of the position of the apparatus must be done to a precision of several microns, ideally, over a linear extent of an inch or so. The invention requires local accuracy only, so that there is no requirement that precision be maintained over the extent of the entire travel of the apparatus, which might be many feet in length.

Similarly, the number of significant bits to be carried in the digitization of the signal is a function of the number of views, the statistical precision of the number of photons in the x-ray sampling, and the desired contrast in the final image. Preferably, twelve to fourteen significant bits worth of data are required for contrast purposes (e.g., a dynamic range of about a factor of several thousands), if the range of attenuation within the views that constitute the local data do not differ by more than a factor of two, the number of views per point is large, (e.g., 30 or more), and the number of spatial resolution elements in depth of the test specimen, i.e., number of layers, is no more than about 100. These required accuracies can be derived from standard reconstructive x-ray imagine analyses, but the addition of specialized processing algorithms, as described below, can change the parametric relationships.

Figure 7B:
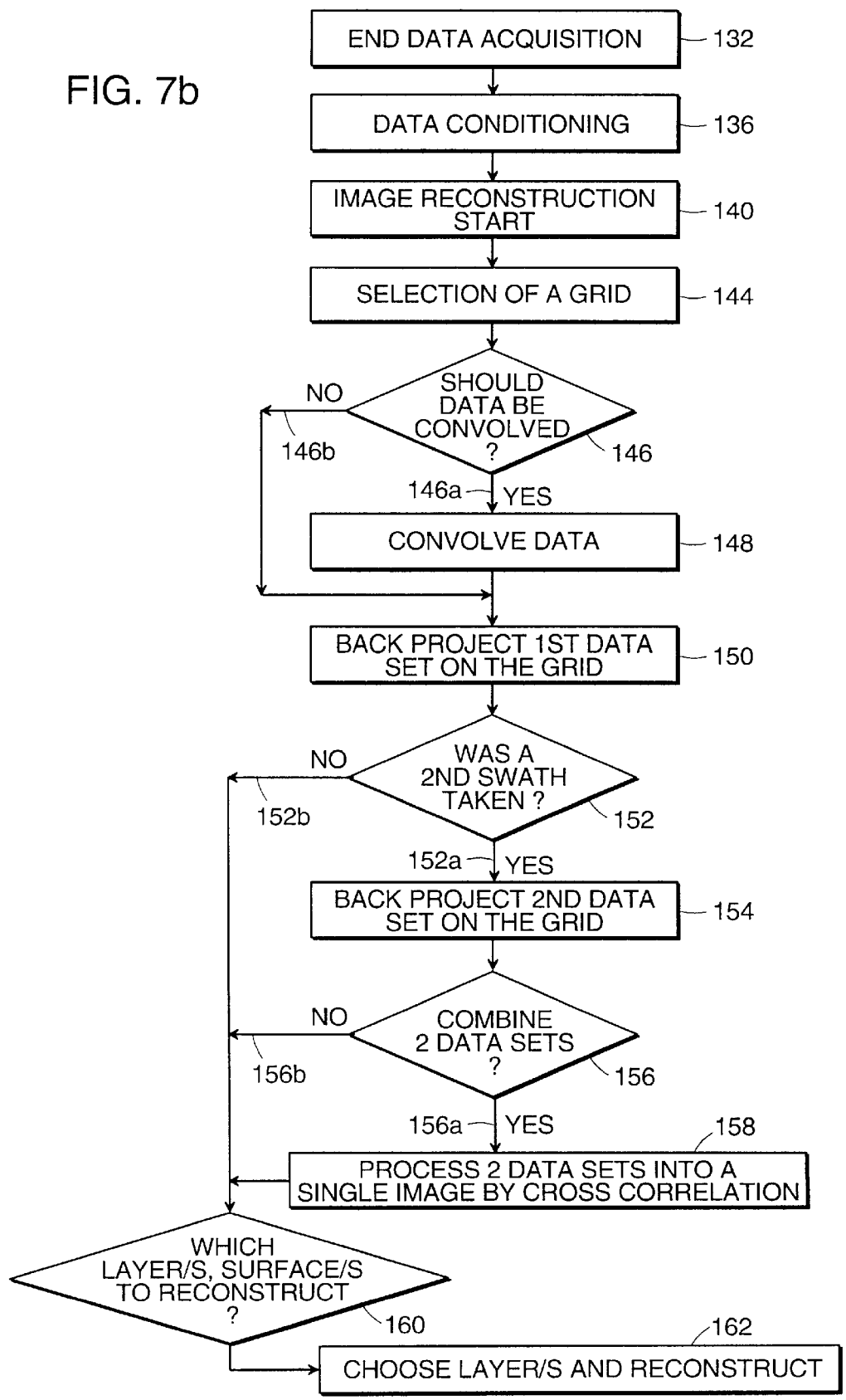

The second step, (step 136, FIG. 7b), data conditioning, includes removing all the instrumental effects from the absorption measurements. The set of operations involved include the following operations which are representative, but not exhaustive of the process: normalization of the absorption data for temporal variations in the x-ray flux, (this is done with the aid of an x-ray flux monitor, which is a small spatially-unresolved x-ray detector that has an unobstructed view to the x-ray generator); interpolation of data for any missed views; and removal of electronic glitches and noise in the data acquisition system. Looking for other errors and glitches is usually straight-forward because the data do not vary considerably from one view/frame to the next, i.e., temporally. In addition, the spatial variation across the detector is usually relatively small for this class of test specimens. Therefore, by setting electronic traps for bad data, most high-frequency, errors and electronic glitches can be automatically detected and discarded.

The third step, (step 140), image reconstruction, starts with substep, (step 144). This step includes selection of the grid on which the data are to be reconstructed, optionally convolving the data with a mathematical kernel, and backprojection of the data. Grid selection is usually based on the geometry of the test specimen. A composite laminate with various layers of woven fibers would most likely utilize a geometry where the surfaces of reconstruction follow the layered structure of the laminate. If the test specimen were flat, an x-y-z coordinate system with the x-z plane parallel to the laminates might be chosen. On the other hand, if the test specimen were a curved section of a cylinder, then an r-theta-z coordinate system might be chosen, with the r-z plane parallel to the test specimen's layers. (It is not necessary to choose the coordinate system this way; the same x-y-z system could be chosen in all cases, and the data for the test specimen later interpolated from that data, as is done later, but it is usually easier to select an appropriate coordinate system in the first place.) The data for each pass will be handled separately, until the end of the process, when the data may be combined.

If preferred, (decision 146, branch 146a), the second substep of reconstruction, (step 148), is convolution with a mathematical kernel. This step 148 is optional but will frequently result in better, more artifact-free images. (Convolution before reconstruction is not done for conventional laminographic techniques). In this step, the data is convolved with a mathematical kernel that emphasizes the high-frequency components of the data, or equivalently, suppresses the low-frequency components. The reason for this convolution is to flatten the image, which can have a very large gradient superposed on it, especially if the various views that went into the construction of the image have large variations in the absorption. The choice of the kernel is directly related to the geometry of the test specimen and the angular coverage of the test specimen as seen by the SDC. In addition, the choice of the kernel depends on the fineness of the spacing between planes, the thickness of the test specimen and the spatial resolution within the test specimen. Considerations of noise and features that bear emphasis (or artifacts that require suppression) also enter into the choice of the kernel. The kernel is almost always expressed in the Fourier spatial frequency domain and is selected empirically; while no single set of rules for selection of the kernel governs, the effect on the final image of various classes of kernels is similar to that class of kernels as known from the computer-tomography convolve-and-backproject algorithms. In addition, the best kernel may not be constant over all views, but may change as a function of angle of the view. One example of a mathematical kernel is the classic Shepp-Logan filter, which utilizes a functional form $f(\omega)=\omega$ in the regime where $\omega$, which corresponds to spatial frequency, is in the range, $0<\omega<\omega_0$. In the regions $f(\omega)=0$, $\omega_0$ is the highest sampling frequency of the source-detector specimen geometry, e.g., the Fourier-space $\omega$ corresponding to 7 cycles/mm for instance, in the spatial domain. If no convolution is performed, (decision 146, branch 146*b*), the processes jumps to step 150, described below.

The third substep of reconstruction is backprojection. Backprojection of the first data pass occurs during step 150. If a second pass is taken, (decision 152, branch 152*a*), backprojection of the second data pass occurs during step 154. If a second pass is not taken, (decision 152, branch 152*b*), the process jumps to step 160. Reconstructing each point of the particular pass on the reconstruction grid involves, for each point in the pass, backprojecting the data, (or optionally, the convolved data), corresponding to the predetermined number of views of that point. By reconstructing each point, for each pass, a grid is built up, layer by layer, until the region of interest of the test specimen is reconstructed. The two reconstructions, corresponding to the two separate data sets, will have many similarities, as various features appear in both reconstructions. However, the two separate reconstructions will be different because the data that went into each are most sensitive to small-scale features whose variations lie along different lines-of-travel between the SDC and the test specimen. In other words, these are two separate image reconstructions, one for each data pass, that have not yet been combined. If desired, the two reconstructions can be viewed together, (decision 156, branch 156*a*), in which case they can be further processed into a single image by a correlation process (step 158). This step will enhance the detectability and appearance of features that lie at an oblique angle to both passes. Otherwise, (decision 156, branch 156*b*), each data set can be viewed separately. If the test specimen is large such that a series of parallel first and/or second passes were taken, then for each pass direction, a series of grids are made and joined into a mosaic to form a grid of the whole test area.

This fourth reconstruction substep, (step 158), cross-correlation of the two orthogonal image data sets, is a step in which fine-scale features that are common to both data sets are used to anchor the combined image. Any standard correlation function, such as a maximization of a cross correlation factor may be used to overlay the two images into a single map, which images features with spatial components in all directions with isotropic contrast. In order to increase the correlation, the parameters to be adjusted might include, for example, magnification, tilt, warp and/or contrast of specific regions. The positions where the correlation is highest form the attach points for the two different data sets. Once these points are chosen, the data added from the two maps are corrected for the parameterization just determined and then added. Any data point can be assigned the same five parameter adjustments in theory. These parameters can be x-y-z offsets and two angles—essentially five variables in free-space—assuming that the entire source-detector combination and test specimen can be considered to perform rigidly over the region of the match. In considering the points, if the assumptions of test/specimen/and geometry rigidity do not hold, a warp factor of the test specimen should also be considered, where a closer set of correlation should be performed over a series of much smaller contiguous regions. If there are no matching features between images formed from the two data passes, correlation will not work, but in such a situation there are no interesting features to detect anyway. The great advantage of image processing of these separate data pieces into a single overall image carrying all the feature information (e.g., by cross-correlation techniques) lies in obviating the need to maintain precise mechanical registration between orthogonal passes.

The fifth reconstruction substep (step 162) includes reconstructing specific layers or surfaces within the reconstructed image. Irrespective of the sources of the image map, a decision 160 must be made: Along which layer(s) or surface (s) within the test specimen should reconstruction be performed? For example, a composite test specimen consisting of sheet layers of woven material separated by resin-dominated material is reconstructed on a set of surfaces (step 162) that are parallel to the woven sheets. The actual determination of the surface could be accomplished through interrogation of an INDERS database to access data corresponding to the chosen region. Another method following the woven layer works empirically: The reconstructed region is sampled by starting from an arbitrary point and then checking the density of that point in adjacent points. If the character (e.g., the weave pattern) of the data sampled is different from that of the specified layer, the program searches other local data for patterns reflecting that of the specified layer. This point is used as the next starting point in the iteration, until all points in the layer have been exhausted. As long as the layers are well-defined and separated from each other, this approach yields a series of surfaces of the composite/laminate material. This method is able to follow arbitrary internal surfaces, whether flat or curved. Any other standard high spatial resolution three-dimensional data function can be performed, (i.e., any quantitative analysis may be used), as if the data were obtained with traditional high resolution positional information over the entire data set.

Figure 1A:
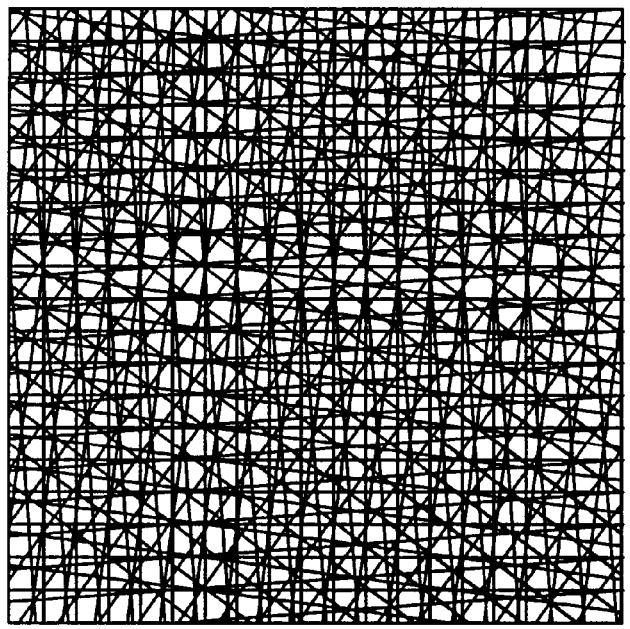
FIG. 1(a) is an illustrative image of a multiple layer test specimen obtained using x-ray techniques.
Figure 1B:
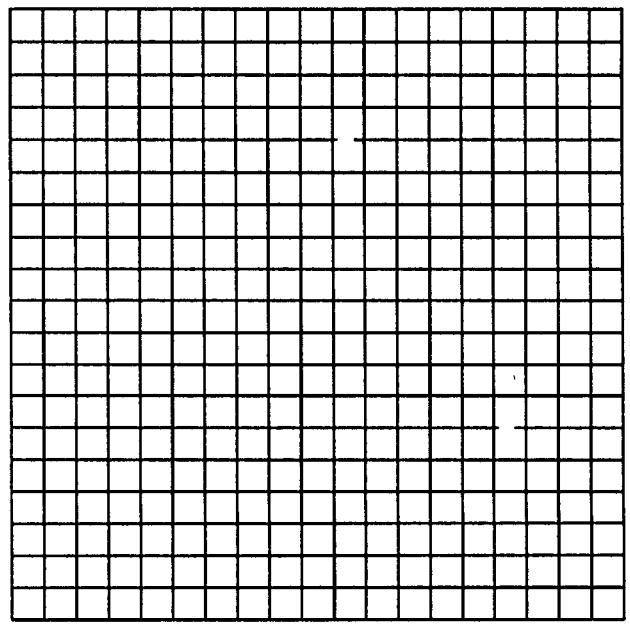
FIG. 1(b) is an illustrative image for a single layer of the multiple layer test specimen obtained using the technique of this invention.

Thus, the technique of the invention can image one or more layers of a multilayer test specimen, through a single scan, two perpendicular scans or (in certain cases three mutually perpendicular scans) of the test specimen, regardless of the orientation of the fibers of each layer, or the orientation of the defects in any layer. FIG. 1(*b*) illustrates an image for a single layer of the multiple layer test specimen, shown in FIG. 1(*a*), which can be obtained using the technique of this invention, where two fiber breaks can be seen.

In sum, the approach of this invention provides an inspection method which requires few motions over an area, typically two, and requires mechanical accuracy only over limited areas, allowing large test specimens to be tested with accuracy even while a composite material is in process. In addition, the approach of this invention permits better inspections at joints and complex regions than is available under current nonreconstructive inspection techniques.

The specific embodiment described is by way of example only, and all the functions described could be performed by dedicated hardware, by software or by a combination of hardware and software. It should be apparent to those skilled in the art that the foregoing is merely illustrative and not limiting, having been presented by way of example only. Numerous modifications and other embodiments are within the scope of one of ordinary skill in the art and are contemplated as falling within the scope of the invention as defined by the appended claims and equivalents thereto.

What is claimed:

1. A tomographic system for imaging the internal structure of a test specimen, comprising:
   an areal detector spaced by a first predetermined distance from the test specimen;
   a source of radiation spaced by a second predetermined distance from the test specimen;
   a mechanical manipulator for creating selective relative movement between the test specimen and the source;
   a control for actuating said source at selected relative positions between the source and the test specimen during a single relative translational pass in a first direction between the test specimen and the source, the source producing radiation during each actuation which impinges a selected volume of the test specimen and projects a two dimensional image of the selected volume onto the detector, successive actuations radiating successive selected volumes, wherein at least adjacent selected volumes partially overlap; and
   a processor for processing the images, the processor reconstructing a selected surface of the test specimen.

2. A tomographic system as in claim 1, wherein the source, detector and test specimen are positioned to produce a magnified image of the selected volume on the detector when the source is actuated.

3. A tomographic system as in claim 2, wherein:
   the test specimen comprises a plurality of points;
   the source radiating consecutive volumes of the test specimen, each from different relative position, there being at least one point which is common to a predetermined number of consecutive volumes imaged from a predetermined number of different relative positions, such that a predetermined number of different images of the at least one point are produced; and
   the processor reconstructing the at least one point in the selected surface from the predetermined number of different images of the at least one point.

4. A tomographic system as in claim 3, wherein the predetermined number of consecutive volumes is a selected fraction of the total number of volumes.

5. A tomographic system as in claim 4, wherein the radiation source radiates with a selected angular width for imaging the at least one point a predetermined number of times from the predetermined number of different relative positions.

6. A tomographic system as in claim 1, wherein the mechanical manipulator is also operative to create selective relative movement between the test specimen and the areal detector.

7. A tomographic system as in claim 1, further having a digitizer for digitizing images from the areal detector, storing the digitized images as a first data set and inputting the digitized data to the processor.

8. A tomographic system as in claim 7, further comprising a database for organizing the first data set according to the geometry of the test specimen.

9. A tomographic system as in claim 8, further comprising a surface choice algorithm for selecting from the database data corresponding to one or more surfaces of the test specimen to be reconstructed, and a reconstruction unit for reconstructing the one or more surfaces using the selected data.

10. A tomographic system as in claim 9, further comprising a quantitative analysis unit for analyzing data of the first data set corresponding to a surface for occurrences of certain features.

11. A tomographic system as in claim 1, wherein the areal detector includes a converter of detected radiation to digital signals.

12. A tomographic system as in claim 11, wherein said converter includes:
   a first converter for converting radiation to visible light;
   a camera connected to the output of the first converter, the camera imaging and converting the visible light image to a video signal;
   a video line connected to the output of the camera; and
   an analog to digital converter connected to the video line output.

13. A tomographic system as in claim 1, wherein the radiation is x-ray radiation.

14. A tomographic system as in claim 1, wherein the source is a microfocus source.

15. A tomographic system as in claim 1, where the test specimen is a composite and the processor reconstructs at least one layer of the composite.

16. A method for producing tomographic images of a test specimen having multiple points, the method comprising steps of:
   (a) setting a source of radiation, an areal detector and a test specimen in a configuration that yields a magnified two dimensional image of an imaged volume on the detector when the test specimen is radiated by the source;
   (b) creating selected relative motion between the source and test specimen to scan the test specimen in a first translational pass;
   (c) actuating the source to selectively image the test specimen during said first translational pass as the source and test specimen are at different relative positions, the radiation from the source, imaging at least one point from a different relative position for each actuating of the source, producing a predetermined number of different images of the at least one point; and
   (d) reconstructing a selected surface of the test specimen point-by-point, for each of the at least one point on the surface being reconstructed, utilizing the predetermined number of images of the at least one point;
   mechanical accuracy between the source/detector combination and the test specimen being maintained during step (b), for at least the period required to image the predetermined number of different images of each said at least one point.

17. A method for producing tomographic images as in claim 16, including steps performed before step (d) of:
   (d1) digitizing the images from the areal detector; and
   (d2) storing the digitized images as a first data set.

18. A method for producing tomographic images as in claim 17, including the step, performed for a test specimen which is wider then said first translational pass, of (e) repeating steps (b) and (c) to make an additional first translational pass parallel to the first translational pass of the test specimen, step (e) being performed a number of times sufficient to cover the full width of the test specimen, each of said first translational passes being separated by a field-of-view for the test specimen.

19. A method for producing tomographic images as in claim 18, further comprising steps of:

(f) repeating steps (b) and (c), and if necessary step (e), to image the full test specimen during one or more second translational passes, the second translational passes being perpendicular to the first translational passes; and (g) digitizing and storing data from the second passes as a second data set, the second data set being uncorrelated with the first data set.

20. A method for producing tomographic images of a test specimen as in claim 19, further comprising a step of (h) processing the first and second data sets into a single image.

21. A method for producing tomographic images of a test specimen as in claim 20, wherein step (h) includes correlating the two data sets by use of precision fiducials.

22. A method for producing tomographic images as in claim 19, wherein step (f) is performed independently of step (c) and without requiring mechanical registration between the first and second translational passes.

23. A method for producing tomographic images as in claim 19, wherein defects detected during the first translational pass are defects having small scale features which lie predominantly in the direction parallel to the first translational pass, and defects detected during the second translational pass are defects having small scale components which lie predominately in a direction parallel to the second translational pass direction, wherein passes in both the first and second directions detect any defects.

24. A method for producing tomographic images as in claim 19, further comprising the steps of:

(i) repeating steps (b) and (c), and if necessary (e) to image the full test specimen during one or more third translational passes, the third passes having at least a significant component perpendicular to the first and second passes; and (j) digitizing and storing the data corresponding to the third passes as a third data set, the third data set being uncorrelated with the first and second data sets.

25. A method for producing tomographic images as in claim 17, wherein step (d2) comprises storing the data in a database in which the data are stored according to the geometry of the test specimen.

26. A method for producing tomographic images as in claim 25, wherein step (d) further comprises steps of:

(d3) selecting from the database data corresponding to at least one surface of the test specimen to be reconstructed; and (d4) reconstructing the surface.

27. A method for producing tomographic images as in claim 26, wherein step (d) further comprises step (d5) of performing quantitative analysis on the data corresponding to the at least one selected surface.

28. A method for producing tomographic images as in claim 26, wherein step (d) further comprises step (d6) of selecting a grid on which data are to be reconstructed, where the grid is aligned to the geometry of the test specimen.

29. A method for producing tomographic images as in claim 16, wherein step (d) further comprises step (d7) of convolving the data set with a mathematical kernel which emphasize the high frequency components of the data, prior to the reconstruction step.

30. A tomographic imaging method as in claim 29, wherein the kernel depends on the geometry of the test specimen, the angular coverage of the test specimen as seen by the source-detector, the fineness of the spacing between planes, the thickness of the test specimen, the spatial resolution within the test specimen, noise and features that require suppression.

31. A tomographic imaging method as in claim 17, wherein step (d) further comprises step (d8) of converting each of the digitized images, representing spatial information, into its conjugate spatial frequency, and applying algorithms that achieve one of (aa) emphasis and (bb) de-emphasis of certain frequency components of the data, prior to the reconstruction step.

32. A method for producing tomographic images as in claim 17, wherein the number of significant bits to be carried in step (d1) is a function of the number of views, the ratio of the spatial resolution in depth versus the thickness of the test specimen, the statistical precision of the number of photons in the x-ray sampling and the desired contrast in the final image.

33. A method for producing tomographic images as in claim 32, wherein the number of data bits is 12–14 for a range of attenuation within the views that constitute the local data not differing by more than a factor of two, and the ideal number of views per point is at a minimum approximately 5 and ideally approximately 30 or more.

34. A tomographic imaging method as in claim 16, wherein during step (b) the relative motion is one of (i) continuous and (ii) stepped.

35. A tomographic imaging method as in claim 16, wherein the predetermined number of different images of the at least one point are a selected fraction of the total number of images which are taken during the first translational pass.

36. A tomographic imaging method as in claim 35, wherein step (a) further comprises the step of setting the source to have a wide angle radiation beam, sufficient for producing the predetermined number of different images of the at least one point, while the source is actuated a predetermined number of times.

37. A tomographic imaging method as in claim 16, wherein the selective relative movement is also between the test specimen and the areal detector, the source and areal detectors moving together.

38. A tomographic imaging method as in claim 37, wherein relative motion is achieved by one of (a) keeping the source and detector stationary and moving the test specimen and (b) keeping the test specimen stationary while moving the source and detector.

39. A tomographic imaging method as in claim 16, wherein the method is a laminographic technique for imaging layers of a composite test specimen, a selected layer of the composite being reconstructed during step (d).

40. A method for producing tomographic images as in claim 16, wherein the method is used to image the test specimen, surface-by-surface.

* * * * *